United States Patent [19]
Gorman

[11] 3,975,248
[45] Aug. 17, 1976

[54] MOLECULAR COMPOSITE STRUCTURES

[75] Inventor: Lee V. Gorman, Dallas, Tex.

[73] Assignee: Chemprobe Corporation, Garland, Tex.

[22] Filed: Sept. 12, 1974

[21] Appl. No.: 505,238

Related U.S. Application Data

[63] Continuation-in-part of Ser. No. 365,478, May 31, 1973, abandoned.

[52] U.S. Cl. ...................... 204/157.1 S; 204/158 S; 260/162 S; 260/429 R; 260/448 R

[51] Int. Cl.[2] ............................................ B01J 1/12

[58] Field of Search ................. 204/157.1 S, 158 S, 204/162 S; 260/429, 448

[56] References Cited

UNITED STATES PATENTS 3,325,386 6/1967 Jurschewitz ................. 204/157.1 S 3,346,472 10/1967 Long ............................ 204/157.1 S

*Primary Examiner*—Howard S. Williams
*Attorney, Agent, or Firm*—Richards, Harris and Medlock

[57] ABSTRACT

Oxygen-containing carbon and silicon compounds having free appendant groups selected from hydrogen, hydroxy, amino, halogen, and oxygen are sintered into a molecular composite by means of a diffusant element of Groups IIIA, IV or VA of the Periodic Table to form novel compositions. These composite compositions are produced by a process which includes contamination of oxygen-containing carbon and silicon compounds with a diffusant element of Group IIIA or VA, or Ge, Sn or Ti of Group IV, and then subjecting the mixture to sintering which includes a high excitation energy and pressure.

30 Claims, No Drawings

MOLECULAR COMPOSITE STRUCTURES

This application is a Continuation-In-Part application of copending U.S. Application Ser. No. 365,478 filed May 31, 1973, now abandoned.

This invention relates to novel compositions. In another aspect, this invention relates to a novel process for incorporating desired chemical and physical properties into certain compounds. In still another aspect, this invention relates to a novel process for producing novel hydrophobic materials.

Chemical synthesis, and particularly polymerization techniques can produce many materials tailored for specific end uses. For example, artificial resins which include silicone resins, olefin polymers fluoropolymers, vinyl resins, acrylic resins, polyesters, polyurethanes, and the like, have gained wide usage in industry. Polymers can be tailored for various end use requirements by utilizing specific monomeric reactants, controlling the molecular weight, and incorporating various reactive or inert groups therewithin. However, in many instances, the resins must be mechanically mixed with filler materials to impart desired physical, chemical, and/or electrical porperties to the resin. The filler materials thus provide properties to known molecular substances, that the substances alone do not possess. For example, various materials are admixed with polymers to provide strength, body, hardness, dielectric properties, water-resistant properties, surface texture properties, and the like.

While additives can indeed impart desired characteristics to known chemical compositions such as resin compositions, the resulting admixtures possess chemical, physical and/or electrical weaknesses of one or more of the constituents in the mixture. This is particularly true when particulate solid material is admixed with resins to provide materials used for various molding, or coating operations. Generally, the particulate material can contribute to the lack of translucence or transparency of the final product as well as incorporating undesirable wear and adhesion problems to the product.

Accordingly, one object of this invention is to provide a novel process for combining certain chemical compounds.

Another object of this invention is to provide novel chemical combinations of dissimilar materials and a process for producing the same.

Another object of this invention is to provide a novel process for producing novel hydrophobic compounds.

Still another object of this invention is to provide a novel combination of normally solid particulate materials with polymeric materials.

According to the invention, primary compounds from a first group selected from compounds having both a tetravalent element and oxygen in the molecular structure and having free appendant groups selected from hydrogen, hydroxy, amino, halogen, and oxygen are diffused with a material comprising a solid element of Group IIIA, or VA, or Ge, Sn and Ti of Group IV, by intimately admixing the materials and subjecting the mixture to a high excitation energy. In addition, compounds of a second group which are selected from other elemental oxides such as beryllium oxide can also be sintered to the molecular composite by means of the diffusant material.

In a specific embodiment of this invention a novel process is provided for producing novel molecular combinations which includes admixing a primary material selected from the group consisting of oxygen-containing carbon and silicon compounds having free appendant groups selected from hydrogen, hydroxy, amino, halogen, and oxygen; and mixtures thereof with a solid element selected from Groups IIIA, VA, and Ge, Sn and Ti of Group IV of the Periodic Table, and thereafter subjecting the resulting mixture to an excitation energy having a frequency above that 10 kilocycles per second and a pressure above about 500 pounds per square inch.

According to another specific embodiment of this invention, oxygen-containing carbon or silicon compounds such as polymeric compounds, which possess hydrogen bonding potentials are sintered by a diffusant which comprises a normally solid element of Groups IIIA; VA; Ge, Sn or Ti of Group IV of the Periodic Table by admixing such compounds with such a Group IIIA, IV, or VA element in finely comminuted form and subjecting the mixture to a high excitation energy to effect a linkage between said compounds and said element.

According to another specific embodiment of this invention, hydrophobic properties are imparted to carbon or silicon-containing compounds which compounds have free hydrogen, hydroxy, amino, halogen and/or oxygen groups by coupling a hydrophobic material such as a methylsilyl fumed silicon dioxide thereto by a diffusant comprising a normally solid element selected from Groups IIIA, VA or Ge, Sn or Ti of Group IV of the Periodic Table.

In accordance with still another specific embodiment of this invention, materials from a third group which includes halogen donors, 1-olefins and vinyl compounds and halogenated derivatives thereof are sintered with materials from the first and second groups by the same above-described diffusant.

Thus, it has been discovered that the above-described molecular composites can be subjected to diffusion conditions which include a high excitation energy and thereby be sintered into composites with different chemical and physical properties. Compounds in the first group, or in the first and second and/or third group can be sintered together by the action of a selected element of Groups IIIA, IV or VA of the Periodic Table. Preferred such chemical compounds within the first group include oxygen-containing compounds of tetravalent elements such as carbon, silicon or sulfur. Compounds within the first group include siloxanes; organosiloxanes; polymers and non-polymers containing carbon and/or silicon and oxygen in the molecular nucleus and having free appendant groups selected from hydrogen, hydroxy, amino, halogen, and oxygen; and mixtures thereof. Examples of suitable polymers in the first group comprise the acrylic polymers which includes the polymers and copolymers of acrylic acid, methacrylic acid, alkyl esters of these acids, and acrylonitrile; the polyesters which include basically the reaction products of di or tribasic acids and di or trihydric alcohols; the polyethers such as polyoxyethylene or polyoxyethyleneoxypropylene; polyurethanes; polysulfides, polysiloxanes; and the organosiloxane polymers, i.e., silicone resins. The most preferred class of the first compounds include chemical compounds which are capable of hydrogen bonding.

The materials referred to as diffusants include the normally solid elements in Groups IIIA and VA, and germanium, tin, and titanium of Group IV of the Periodic Table as illustrated on page B-2 of the Handbook of Chemistry and Physics, Chemical Rubber Publishing Company (1964). It is noted that the term "normally solid" as used in this specification means the physical state of being non-gaseous at standard temperatures and pressure conditions. The most preferred diffusants used in the scope of the subject invention are the substantially pure elements of Groups IIIA, VA and germanium, tin and titanium of Group IV of the Periodic Table. In a lessor preferred embodiment of this invention, the diffusant can be added to the process as a compound. In the latter instance, the most preferred diffusants can be selected from the group which consists essentially of hydrides, oxides, hydroxides, halides, nitrides, sulfides, and oxyhalides of the normally solid elements of Groups IIIA, VA, and germanium, tin and titanium of Group IV of the Periodic Table. The diffusant is most preferably in a finely comminuted form when contacted with the materials from another group or groups in accordance with the subject invention. More specifically, the diffusants should have a particle size no larger than about 500 microns and preferably 10 microns and smaller. Generally, the smaller the particle size of the diffusant, the more efficient will be the sintering process. Thus when the preferred pure element is used as the diffusant within the scope of this invention, it can have a particle size from about 500 microns to atomic size.

The second group includes the normally solid elemental oxides formed from elements other than those set forth in Groups IIIA, VA, and IVA and titanium in Group IVB of the Periodic Table. Particularly preferred oxides are those elements in groups IIA, IB-VIIB and VIII of the Periodic Table, for example oxides of beryllium, vanadium, chromium, manganese, iron, cobalt, nickel, copper, and zinc.

It is possible in accordance with this invention to sinter a material from the first group, such as one of the polymeric materials set forth above with another solid material from the first group, or the third group. Thus, various solid elemental oxides, silicates, carbonates, and sulfates, for example, can be combined with polymeric materials set forth above. A particularly preferred solid material which can be used in the scope of this invention is alkyl silyl fumed silicon dioxide and particularly the hydrophobic trimethyl silyl fumed silicon dioxide which can be represented by the schematic formula set forth below:

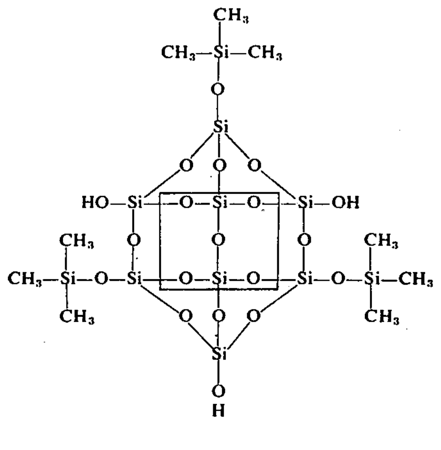

-continued

X = a positive integer

This material is extremely hydrophobic and can be sintered with materials in the first group in accordance with this invention to thereby form stable water repelling compositions.

It is noted that fumed silicon dioxide is produced by hydrolyzing pure silicon tetrachloride vapor in a flame of purified hydrogen and oxygen as set forth below:

$$SiCl_4+2H_2+O_2 \xrightarrow{1800°C} SiO_2+4HCl$$

In the process, molten spheres of silica are first formed. These spheres vary in average diameter from 7 to 14 millimicrons. These molten silica spheres collide and fuse with one another to form three-dimensional branched chain aggregates. Next, the materials are reacted with silane and then the trimethyl silyl group is formed on the surface of the base fumed silicon dioxide particles. The reaction changes the surface characteristics of the silicon dioxide from hydrophilic to hydrophobic.

In addition, it is possible in accordance with another embodiment of this invention, to sinter materials from the first and second groups with materials from a third group. Materials within the third group include halogenating agents such as $Cl_2$, $F_2$, $Br_2$, $I_2$, and halogen-containing acids, halogenated hydrocarbons, halogenated hydrocarbon phosphates, 1-olefins, vinyl compounds and halogenated derivates thereof, such as ethylene, tetrafluoroethylene, propylene, vinyl chloride, vinyl toluene, styrene, and the like.

The amount of sintering between either similar or dissimilar materials from the first group, the second group (if desired), the third group (if desired), is basically governed by the amount of the diffusant material which is added to the mixture. In general, the amount of diffusant material which is added to the mixture can range from as low as about 1 part per million up to and including the maximum stoichiometric amount which includes one-third of the total molar quantity of the materials from the first, second and third groups for the Group IIIA containing diffusants; one-fourth of the total molar quantity of the material from the first, second and third groups for the Group IV containing diffusants and one-fifth of the total molar quantity of the materials from the first, second, and third groups for the Group VA containing reactants. The material from the diffusant group is typically present in amounts of 15–20 parts per million of the reaction mixture.

The sintering association can occur in any fluid medium, for example, for liquid or solid materials, the sintering can occur within the solution phase or dispersed liquid phase in the presence of a diluent which is nondeleterious to the sintering. The choice of diluent will depend somewhat on the nature of the selected materials but generally, suitable diluents include water, halogenated hydrocarbon solvents, and aliphatic and aromatic hydrocarbon solvents, and the like. Alternately, if the selected materials are particulate solids, they can be suspended together in a gaseous stream and reacted in accordance with this invention. Any gaseous diluent which is nondeleterious to the reaction can be used in the scope of this invention. Suitable such diluents include air, nitrogen, argon, helium and the like.

The amount of diluent can be varied as desired. Generally the amount of diluent can range from 0.5 to about 100 volumes per volume of total solids material.

In most instances, the sintering preferably is carried out in the presence of a metallic adjuvant material. Suitable such adjuvants include precious metal alloys of platinum and rodium or any specific precious metal or combination that is capable of high thermal levels without melting or deforming and has a thermal conductivity below about $$0.3 \frac{Cal/cm^2}{cm\text{-}°C\text{-}sec}$$

such adjuvants are located at such a position in the process where maximum energy levels exist and are imparted to the selected materials and the diffusant for sintering.

The reaction is preferably carried out in accordance with this invention by combining a compound or compounds from the first group with one or more compounds from the second group and (one or more compounds from the third group, if desired) with a specific diffusant in a diluent and forming an intimate admixture thereof. The mixture is thereafter subjected to a high excitation energy. Preferably, the sintering occurs at a pressure above 500 psig and generally occurs within an operating range of 500–15,000 psig. In addition, a high excitation energy of above about 10 kilocycles per second is thereafter imparted upon the composite mixture. Generally, satisfactory results have been obtained by utilizing an excitation energy in the range of 10–100 kilocycles per second. The excitation energy can be basically acoustical energy, light energy, radio energy, radar energy or can originate from any other suitable source which will impart the high frequency to the composite mixture. Suitable results have been obtained thus far by utilizing homogenizer apparatus for imparting the excitation energy to the composite mixture. Suitable such homogenizers are sold under the trademark of "Sonolator" by Sonic Corporation, Norwalk, Connecticut. Other suitable homogenizers which can be utilized in the scope of this invention are sold under the trademark of GAULIN by Gaulin Corporation, Everett, Massachusetts.

The above-described apparatus functions to impart high energy kinetics to the reaction mixture in the form of acoustics, pressure and mass acceleration. The above-described Sonolator apparatus pumps a jet of the mixture at high pressures through an orifice against a blade-like obstacle immediately in the jet-stream path. It is noted that the blade-like obstacle can carry a coating of the above-described metallic adjuvant. The fluid mixture itself oscillates in a stable vortexing pattern in the ultrasonic frequency range which, inturn, causes the obstacle and other members in the area to resonate. The net result is a high level of cavitation, turbulence and shear. The fluid is subjected to a high natural frequency in excess of 10,000 cycles per second.

The above-described Gaulin homogenizers function by initially pressurizing the fluid medium in a pump section. The fluid then enters a homogenizing section from the pump section at a high pressure but at a very low velocity. The fluid at high pressure enters a controlled clearance area between a homogenizing valve and a seat. At this point, energy which has been stored as pressure is instantaneously released as a high velocity stream which can be in excess of 900 feet per second. In the high velocity area between the homogenizing valve and valve seat, the fluid is subjected to intense turbulence, hydraulic shear and cavitation. The fluid then emerges from the controlled clearance area and impinges with shattering force and change of direction upon an impact ring. During this process, the fluid is subjected to a high natural harmonic frequency, e.g., 21,000 cycles per second. Furthermore, if desired, the impact ring can be made of or be coated with the above-described metallic adjuvant.

Generally, the materials need only be subjected to the high excitation energy for a period of less than one second. A typical diffusion or sintering time is about $10^{-9}$ seconds. The sintering process can be carried out at any convenient temperature. Much heat is usually generated as a result of frictional energy transfer in the fluid. Generally, the sintering is carried out with the materials initially at ordinary room temperature conditions.

As a general rule, the lower the molecular weight of the materials in the above-described first, second and third groups, the more extreme the conditions should be, e.g., higher pressure and excitation energy when contact is made with the diffusant. Furthermore, when sintering dissimilar compounds of different molecular weights, and particularly when there is a relatively great difference between the molecular weights thereof, (e.g., one compound is 50% heavier than the other) it is preferable, and many times necessary, to couple the diffusant and the low molecular weight compound and then sinter the high molecular weight compound or compounds to the resulting composite. This is done by initially contacting only the low molecular weight compound and the diffusant under the above-described high pressure and high excitation energy conditions until the diffusion is complete. Thereafter the high molecular weight compound is added to the diluent and then the resulting mixture is subjected to the high pressure and high excitation energy conditions until the sintering is complete. This sequence can be repeated additional times for even higher molecular weight compounds. Thus, the pressure and excitation energy which is sufficient to couple any specific compound at the first, second and third groups with a specific diffusant will vary with the individual material, but generally the heavier the compounds, the milder the required conditions. All such materials can be coupled at pressures above about 500 psig and generally at a pressure in the range of from 500 to 15,000 psig and at excitation energies above about 10 kilocycles per second and generally at an energy level within the range of 10–100 kilocycles per second. The change in physical properties of the subject materials will readily indicate when the sintering is complete.

I am not certain of the exact diffusion and sintering mechanism involved in this process, but it is clear that there exists a coupling or joinder of the materials in the first, and/or second, and/or third groups with the diffusant to form composite compositions with physical properties not possessed by the starting materials and diffusant. Thus, while I am not certain of the exact diffusion and sintering mechanism involved in the novel process, it is theorized that the Group IIIA, IV or VA diffusant causes composite molecular sintering through an electron sharing or ionic linkages (covalent bonds) or electron bonding at appropriate sites on different molecules of the other selected materials. This sintering can be schematically depicted as follows with the Me illustrated as a Group IIIA element and A and B as different molecular species from the first group:

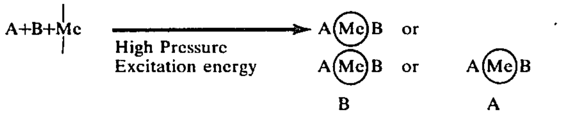

A specific example of what is believed to be the diffusion and sintering mechanism which proceeds in accordance with a preferred embodiment of this invention which comprises the sintering between trimethylsilyl fumed silicon dioxide schematically shown as $(CH_3)_a(-SiO)_bOH$, and dimethyl polysiloxane schematically shown as $(CH_3)_x(SiO)_yOH$, and aluminum diffusant as follows (the elliptical symbols illlustrating what is believed to be the jointer or sintering points):

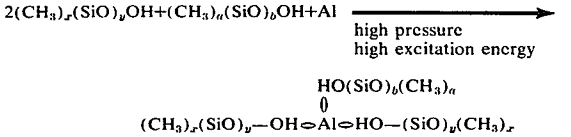

The resulting product can be applied to any suitable substrate such as wood, fibrous materials including paper and textiles, ceramics, and the like, and dried to form a very tenaceous transparent coating which is extremely hydrophobic.

Another specific example of what is believed to be the diffusion and sintering mechanism of another process which is carried out in accordance with the subject invention between sodium methyl siliconate and trimethylsilyl fumed silicon dioxide, and germanium is set forth below:

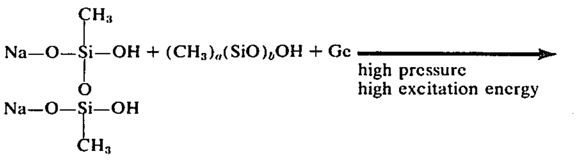

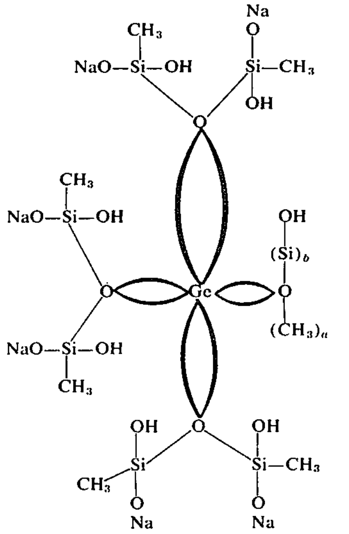

This molecular product can be utilized in a water or alcoholic carrier and incorporated into settable materials such as Portland cement or concrete or plaster of paris mix, for example, to impart water repellency into the hydrated and hardened product.

Still another example of what is believed to be the diffusion and sintering mechanism between selected materials in the first and third groups with specific diffusant in accordance with the subject invention is set forth below. This comprises sintering of 1-dimethyl, 2-trimethyl disiloxanol, Gallium and tetrafluoroethylene.

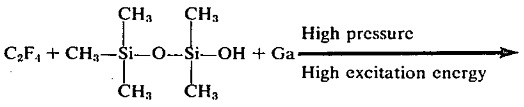

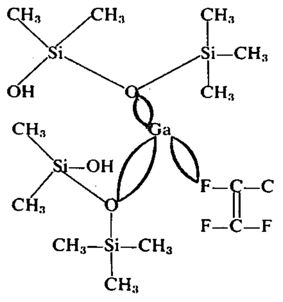

This product demonstrated not only hydrophobic characteristics for water and oil repellancy, but also showed waterproofness on porous fibrous materials.

The following examples are given to better facilitate the understanding of this invention and are not intended to limit the scope thereof.

EXAMPLE 1

Initially, 55 gallons of perchloroethylene were added to a mixing container. Next, during constant admixing 25 pounds of dimethylpolysiloxane were added to the perchloroethylene and dissolved therein. While the stirring was continued, 7.2 pounds of trimethylsilyl fumed silicon dioxide was added to the solution. The trimethylsilyl fumed silicon dioxide is a material sold under the trademark of silanox 101 by Cabot Corporation and contains about 3.4 weight percent carbon. After this, 3 grams of aluminum powder having a particle size of about 3–10 microns was added to the mixture. The solution was pressurized to 1000 psig and passed through a Gaulin Model 15M-8TA homogenizer wherein it was subjected to a natural harmonic frequency of about 21 kilocycles per second. The resulting solution had a pale blue cast and contained only a slight precipitate. The amount of precipitate indicated that the sintering was about 80% complete. The run was repeated except at 2000 psig and the solution produced had a pale blue cast with only a trace of precipitate which indicated a 90–95% complete sintering between the dimethylpolysiloxane and the trimethylsilyl fumed silicon dioxide.

The run was repeated 6 more times at 3000, 4000, 5000, 6000, 7000, and 8000 psig, respectively. In each instance, the resulting solutions had a pale blue cast with absolutely no trace of precipitate. Samples of the solution from these latter runs were passed through a No. 588 Schleicher and Schuell filter. No particulate matter remained on the filter. A sample of a control solution having the same proportions of perchloroethylene, dimethylpolysiloxane, trimethylsilyl fumed silicon dioxide and aluminum powder was thoroughly admixed in a conventional mixing tank and then filtered with a No. 588 Schliecher and Schuell filter. The filter retained all of the trimethylsilyl fumed silicon dioxide and aluminum.

Next, the above solution produced at 3000 psig was sprayed on the side of a brick building made of 8″ × 4″ brick in the amount of 1 gallon to 800 square feet of brickwork. The solution was allowed to dry on the surface of the brickwork. After the solution had dried, there was no visible residue on the surface of the brickwork. The brickwork was totally resistant to the penetration of liquid water. Next, a sample of the above-described control solution which was not passed though the homogenizer was sprayed on similar brickwork. The solution dried and formed a white haze of the trimethylsilyl fumed silicon dioxide and aluminum powder which could be easily wiped from the brickwork.

EXAMPLE 2

Initially 75 grams of a well known fire retardant Tris (2,3-dibromopropyl) phosphate was admixed with 750 grams perchloroethylene and .1 gram aluminum powder having a particle size from about 3–10 microns. The mixture was processed at 7000 psig in the Gaulin Homogenizer Model No. SMD15M-8TA descirbed in Example 1. The resulting sintered product was applied to wood. Also, an identical mixture without the aluminium yet processed the same was applied to another sample of the same wood. After the solvents had evaporated and the material had air cured for 24 hours a flame test was performed. The first sample would not burn even with flame applied. the second sample would burn with flame applied, but would extinguish the flame within 10 seconds after the flame was removed. The first sample demonstrated to be far superior as a fire retardant, probably because of the organizing nature of the diffusant on this particular molecule.

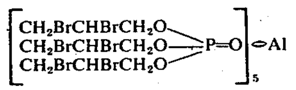

The diffusant can be changed to control the number of molecular families sintered by this diffusion technique.

EXAMPLE 3

Next, 10 pounds of a solution sold by Union Carbide as R-20 and which comprises an aqueous alcoholic solution containing 20 weight percent of sodium methylsiliconate was admixed with 0.36 pounds of trimethylsilyl fumed silicon dioxide which is sold by Cabot Corporation under the trademark of Silanox 101. The materials were thoroughly admixed. Next, 1 gram of powdered germanium having a particle size of less than about 10 microns was stirred into the mixture. The mixture was passed through a Model HT-HP 146 Sonolator homogenizer at 1200 psig which imparted about 10 kilocycles per second of acoustical energy into the solution. The resulting product was clear with a crystal lustre and contained no sediment. Next, several 1 pound samples of a dry concrete mix comprising a standard blend of Portland cement, sand, and coarse aggregate were placed in several sample receptacles. Next, water was admixed with each of the 1 pound samples in an amount which was 20 percent less than the recommended amount for the cement mix. The resulting mixtures appeared to be moist particulate masses. Next, 1 gram of the above-identified solution was added to each of the concrete water mixes and admixed therein. Immediately, the mix was wetted and fluidized. After each sample was thoroughly admixed, it was allowed to set for 3 days at ambient temperatures wherein it was maintained at a temperature in the range of from about 65 to about 80°F. Next, each of the said samples was removed from its container and allowed to set for 3 to 4 more days. After this, each sample was weighed and then immersed in water for 48 hours and removed from the water and weighed again, and it was found that each cement sample absorbed less than 1 weight percent water based upon the weight of the sample. In addition, control samples comprising 1 pound of the same standard concrete mix were made up utilizing the recommended amount of water and allowed to set under the same conditions as the samples set forth above. These samples were then weighed, and then submerged in water for 48 hours and weighed again. It was found that each of the samples gained from 12 to 15 weight percent water, based upon the weight of the sample.

While this invention has been described in relation to its preferred embodiments, it is to be understood that various modifications thereof will now be understood by one skilled in the art upon reading the specification and it is intended to cover such modification as fall within the scope of the appended claims.

I claim:

1. The process comprising admixing a compound selected from a first group which consists of compounds having a tetravalent element and oxygen in the molecular nucleus and free appendant groups selected from hydrogen, hydroxy, amino, halogen, and oxygen, with a diffusant selected from the normally solid elements in Groups IIIA and VA and germanium, tin and titanium in Group IV of the Periodic Table and subjecting the resulting mixture to a pressure above about 500 pounds per square inch and an excitation energy having a frequency above about 10 kilocycles per second to thereby couple said compound and said diffusant.

2. The process of claim 1 wherein said tetravalent element is selected from the group consisting of carbon, silicon, and sulfur.

3. The process of claim 1 wherein said resulting mixture is subjected to a pressure in the range of about 500 pounds per square inch to about 15,000 pounds per square inch and an excitation energy having a frequency between about 10 and about 100 kilocycles per second.

4. The process of claim 1 wherein said first group is selected from oxygen-containing carbon or silicon compounds having free appendant groups selected from hydrogen, hydroxy, amino, halogen, and oxygen.

5. The process of claim 4 wherein two different compounds from said first group are admixed with said diffusant element and thereafter are subjected to said pressure and excitation energy.

6. The process of claim 5 wherein said two compounds froms said first group comprise an organosiloxane and trimethylsilyl fumed silicon dioxide.

7. The process of claim 1 wherein said diffusant element is in comminuted form and has a particle size no larger than about 500 microns.

8. The process of claim 1 wherein said mixture is subjected to said pressure and excitation energy in the presence of a metallic adjuvant which has a thermal conductivity below about $$0.3 \frac{Cal/cm^2}{cm\text{-}°C\text{-}sec}.$$

9. The process of claim 8 wherein said metallic adjuvant comprises platinum.

10. The process of claim 1 further comprising admixing a compound selected from a second group which consists of solid elemental oxides, with said cmpound from said first group and said diffusant before said mixture is subjected to said pressure and excitation energy.

11. The process of claim 1 further comprising admixing a compound selected from another group consisting of halogenating agents, halogen containing acids, halogenated hydrocarbons, halogenated hydrocarbon phosphates, 1-olefins, vinyl compounds, and halogenated derivatives thereof with said compound from said first group and said diffusant before said mixture is subjected to said pressure and excitation energy.

12. The process of claim 1 wherein said resulting mixture is formed by adding said first compound and said diffusant to a diluent.

13. The process of claim 12 wherein said diluent is present in said mixture in an amount from about 0.5 to about 100 volumes per volume of total solid materials therein.

14. The process of claim 13 wherein said diffusant is present in said mixture in an amount of at least 1 part per million.

15. The process of claim 14 wherein said diluent is a liquid.

16. The process of claim 1 wherein said diffusant element is added to said mixture in a compound selected from the group consisting of hydrides, oxides, hydroxides, halides, nitrides, sulfides, and oxyhalides of the normally solid elements in Groups IIIA, VA, and germanium, tin and titanium in Group IV of the Periodic Table.

17. A process of sintering a diffusant selected from elements in Groups IIIA and VA and germanium, tin and titanium in Group IV of the Periodic Table to a compound of a first reactant group which consists of compounds having a tetravalent element and oxygen in the molecular nucleus, and free dependent groups selected from hydrogen, hydroxy, amino, halogen, and oxygen; and to a compound selected from compounds in a second group which consists of elemental oxides, and compounds in a third group consisting of halogenating agents, halogen containing acids, halogenated hydrocarbons, halogenated hydrocarbon phosphates, 1-olefines, vinyl compounds and halogenated derivatives thereof by forming a mixture of said diffusant sand said compounds and then subjecting the resulting mixture to a pressure above about 500 pounds per square inch and an excitation energy having a frequency above about 10 kilocycles per second to thereby couple said diffusant to said compound.

18. The process of claim 17 wherein said resulting mixture is subjected to a pressure in the range of about 500 pounds per square inch to about 15,000 pounds per square inch and excitation energy having a frequency between 10 and about 100 kilocycles per second.

19. The process of claim 17 wherein said diffusant is in comminuted form and has a particle size no larger than about 500 microns.

20. The process of claim 17 wherein said mixture is formed by adding said diffusant and said compound to a diluent.

21. The process of claim 20 wherein said diluent is present in said mixture in an amount from about 0.5 to about 100 volumes per volume of total solid materials therein.

22. The process of claim 21 wherein said diffusant is present in said mixture in an amount of at least about 1 part per million.

23. The process of claim 22 wherein said diluent is a liquid.

24. The process of claim 23 wherein said diffusant is aluminum powder and said compound is Tris (2,3-dibromopropyl) phosphate.

25. The process of claim 17 wherein said compounds are sodium methylsiliconate and trimethylsilyl fumed silicon dioxide.

26. The process of claim 25 wherein said diffusant is Gallium.

27. The process of claim 26 wherein said diffusant is germanium.

28. The process of claim 26 wherein said diffusant is aluminum.

29. The process of claim 26 wherein said compounds are 1-dimethyl-2-trimethyl disiloxanol and tetrafluoroethylene and said diffusant is Gallium.

30. The process of claim 17 wherein said compounds have different molecular weight and said diffusant is initially admixed only with said compound having the lower molecular weight and then subjected to said pressure and excitation energy to form an intermediate sintered composite therebetween and thereafter said compound with the high molecular weight is added to the intermediate sintered molecular component and again subjected to said pressure and high energy conditions to form said sintered molecular composite.

* * * * *

PO-1050
(5/69)

UNITED STATES PATENT OFFICE
CERTIFICATE OF CORRECTION

Patent No. 3,975,248 Dated August 17, 1976

Inventor(s) Lee V. Gorman

It is certified that error appears in the above-identified patent and that said Letters Patent are hereby corrected as shown below:

Col. 1, line 25, "porperties" should be --properties--.

Col. 2, line 11, "about that" should be --above about--.

Col. 3, line 8, "temperatures" should be --temperature--.

Col. 5, line 58, "inturn" should be --in turn--;
line 62, "natural frequency" should be --natural harmonic frequency--.

Col. 7, lines 17 and 18, "$(-SiO)_b$" should be --$(SiO)_b$--.

Col. 9, line 38, "descirbed" should be --described--.

Col. 11, line 6, "froms" should be --from--;
line 24, "cmpound" should be --compound--.

Col. 12, line 8, "sand" should be --and--.

Signed and Sealed this

Twenty-first Day of December 1976

[SEAL]

*Attest:*

RUTH C. MASON
*Attesting Officer*

C. MARSHALL DANN
*Commissioner of Patents and Trademarks*